United States Patent [19]
Montgomery

[11] Patent Number: 6,074,662
[45] Date of Patent: Jun. 13, 2000

[54] PROTEINACEOUS ANIMAL CHEW WITH DENTALLY THERAPEUTIC CATION

[76] Inventor: Robert E. Montgomery, P.O. Box 487, Fairview Rd., Monterey, Mass. 01245

[21] Appl. No.: 08/698,475

[22] Filed: Aug. 15, 1996

Related U.S. Application Data

[60] Provisional application No. 60/002,345, Aug. 15, 1995.

[51] Int. Cl.$^7$ ........................................ A61K 9/68
[52] U.S. Cl. ...................... 424/442; 424/54; 424/405; 424/407; 424/410; 424/48
[58] Field of Search ................ 424/48, 54, 405, 424/407, 410, 439–442

[56] References Cited

U.S. PATENT DOCUMENTS

| | | | |
|---|---|---|---|
| 4,568,540 | 2/1986 | Asano et al. | 424/52 |
| 5,200,194 | 4/1993 | Edgrern et al. | 424/473 |
| 5,329,881 | 7/1994 | O'Rourke | 119/710 |
| 5,468,728 | 11/1995 | Sawai et al. | 574/12 |
| 5,700,651 | 12/1997 | Boyer | 424/52 |

FOREIGN PATENT DOCUMENTS

| | | | |
|---|---|---|---|
| 0 272 968 | 6/1988 | France | A61K 9/22 |
| 89/00379 | 1/1989 | WIPO | A01K 15/00 |
| 94/14424 | 7/1994 | WIPO | A61K 9/68 |

OTHER PUBLICATIONS

Derwent Publications Ltd., London; AN 90-137087.

*Primary Examiner*—Neil S. Levy
*Attorney, Agent, or Firm*—Bromberg & Sunstein LLP

[57] ABSTRACT

This invention relates to chewable objects for animals which contain, as a dentally therapeutic ingredient, one or more cationic substances. The inventive therapeutic animal chews are of sufficient durability to allow for a chewing cycle long enough for the release of the aforementioned cationic substances into saliva. Furthermore, the inventive animal chews may contain an effective amount of a counter-ionic compound, such as an alkali metal salt, to allow for rapid solubilization of said cationic antimicrobial substance into the saliva of an animal chewing thereupon, especially when delivered or carried on a carrier having a negatively charged surface.

1 Claim, No Drawings

PROTEINACEOUS ANIMAL CHEW WITH DENTALLY THERAPEUTIC CATION

CROSS REFERENCE

This application claims priority from provisional application Ser. No. 60/002,345, filed Aug. 15, 1995.

TECHNICAL FIELD

The invention is directed to methods and compositions for delivery of therapeutic agents to an animal by oral administration.

BACKGROUND ART

It is known that the dental health of dogs or other domestic animals is often deficient owing to the impossibility of achieving an effective brushing of their teeth with suitable dental products in a way comparable to that in humans.

A number of therapeutic proteinaceous animal chews have been described in the prior art to address this problem. The therapeutic effect from these prior art compositions or devices comes primarily from the physical act of chewing an object to provide an abrasive effect on the teeth prior to swallowing the compositions. The act of regularly chewing an object (such as rawhide) sufficiently rigid to allow for an oral residence time of greater than thirty seconds or so has been shown to result in reduced tartar accumulation compared to a quickly consumable object, such as a biscuit (Lags, et al J. Am. Veterinary Medical Ass, 197, pp 213–219 (1990)).

Simone et al. U.S. Pat. No. 5,296,209, reported on an attempt to clean an animal's teeth through providing a foodstuff with a texture that allows for the animals tooth, during the act of chewing, to penetrate relatively deep into the food particle before it breaks apart into smaller particles. By doing so, the tooth surface is mechanically abraded by the food particle for a longer period of time than would be possible with a hard, readily breakable food particle. The disadvantage to this approach to companion animal dental hygiene is that only physical accumulation such as tartar, and perhaps some plaque structure, are removed. There is little offered in the way of a truly therapeutic or preventative effect.

These animal chews may in certain instances contain therapeutic compositions in addition to the chew itself. Compositions that have been incorporated into the animal chew may be identified as belonging to one of two categories. The first category is that of enzymatic compositions exemplified by Montgomery U.S. Pat. No. 5,310,541. Enzymatic compositions have been found to have limited antimicrobial effect. The second category is that of non-enzymatic compositions associated with the animal chews.

For example, Stacey, U.S. Pat. No. 5,296,217, described the use of a hexametaphosphate salt added to a consumable animal treat or foodstuff in order to prevent tartar accumulation in domestic animals. Not only is the residence time of the salt too short to have a significant therapeutic effect in the oral cavity of the animal, but furthermore, the hexametaphosphate is not antimicrobial. In Spanier et al., U.S. Pat. Nos 5,114,704 and 5,011,679, a rawhide carrier coated with an inorganic pyrophosphate compound was described for purposes of preventing tartar accumulation in dogs. Pyrophosphate is a calcium chelator that limits the accumulation of tartar and reduces the tartar build-up that has occurred. However, this composition lacks antimicrobial properties.

There are a number of cationic antimicrobial agents that have been utilized in toothpastes for human dental care. These agents strongly associate with protein and are not readily released from proteinaceous substrates.

There is an unmet need for an animal chew that has effective antimicrobial properties in the oral cavity of an animal.

SUMMARY OF THE INVENTION

The invention satisfies the above need. A novel animal oral care composition is provided that includes a carrier having a negatively-charged surface and an effective dose of a therapeutic composition for achieving antimicrobial activity in the oral cavity of the animal, wherein the therapeutic composition contains at least a cationic antimicrobial substance and is in a saliva soluble form positioned close to or at the surface of the proteinaceous carrier. A method is further provided for providing dental health in an animal, including obtaining an animal oral care composition as described above and administering the composition to the animal in a form that will be voluntarily chewed by the animal.

DETAILED DESCRIPTION

The invention provides a composition and method directed to the dental health and well-being of animals and includes the following features. Firstly, the composition is safe for consumption, much as a foodstuff or animal feed would be; secondly, human intervention is not required in the companion animal oral care process; thirdly, in order to satisfy the self-administration rule, the composition in association with a carrier, is sufficiently palatable for the animal to maintain its interest in consuming the material; fourthly, the residence time of the composition and the carrier is sufficient to permit the desired therapeutic effect; and fifthly the therapeutic substance is readily released into saliva upon being chewed.

The present invention has accomplished all these criteria in a novel formulation. According to the invention, a carrier is utilized that has a negative surface charge. The carrier may be formed from natural or synthetic substances, and further may be inherently negatively charged, or may be coated by a reagent that imparts the negative charge to the surface of the carrier. The carrier should persist in the oral cavity of the animal for a minimum residence time of at least 1 minute. Furthermore, the carrier itself should be palatable for the animal such that the interest of the animal in the carrier is maintained.

The carrier provides a means for introducing the therapeutic agent into the oral cavity. The therapeutic substance is located on or near the surface of the chewable object in order for intimate contact between the moisture of saliva and the therapeutic substance to occur almost immediately upon the start of the chewing cycle so as to minimize the possibility that the therapeutic substance will be consumed with the chew, rather than being released in to the oral cavity.

An embodiment of the invention describes a formulation that utilizes a proteinaceous animal chew such as rawhide, and a dentally therapeutic cation, (in this example, chlorhexidine) that is maintained on the surface of the chew on the basis of charge attraction. The cationic antimicrobials become strongly bound to negatively-charged surfaces containing negatively charged moieties such as carboxylic, phosphate and sulfate moieties by forming salt bridges. Cationic antimicrobials that are released from the carrier in the presence of saliva are observed to have a long duration of action, due to their retention and adherence to the negatively-charged surface in the oral cavity, e.g., enamel hydroxyapatite, acquired pellicle protein, and the oral mucosa.

In a preferred embodiment, the cation is rapidly solubilized in the saliva of the oral cavity when the cation is combined with or deposited on the chew in the presence of an alkali metal salt such as sodium gluconate. It has unexpectedly been found that the presence of the alkali metal salt effectively prevents the cationic compound from precipitating or otherwise adhering to the proteinaceous carrier, thus rendering it readily soluble in saliva during the chewing cycle. The invention is not limited to a solubilization process that utilizes an alkali metal salt. Alternative secondary agents are contemplated that provide a means to readily release cations into saliva. Thus, the therapeutic cation is released into the salivary solution during the chewing cycle, rather than carried into the intestinal tract as a result of being bound irreversibly to the carrier.

Cationic antimicrobials contemplated to have utility in the invention include chlorhexidine diacetate, chlorhexidine digluconate, cetylpyridinium chloride, domiphen bromide, benzalkonium chloride, benzethonium chloride, and alexidene.

Alkali metal salts having utility in the invention include sodium and potassium salts of hydrochloric acid, hydrobromic acid, gluconic acid, and acetic acid.

Auxiliary ingredients such as flavorants and film-forming agents may be included in the compositions to provide a specific palatability or coating effect respectively. In particular, film formers such as hydroxypropylcellulose, carrageenan and polyvinylpyrrolidone may provide for a more uniform coating of the carrier surface with the inventive compositions. The auxiliary ingredients are not essential for the practice of the invention.

An example of the inventive composition is prepared as follows:

EXAMPLES

Example 1

Preparation of a rawhide chew having antimicrobial activity 5 lbs of dried rectangular rawhide chews were basted with the following solution using a spray bottle:

| | |
|---|---|
| Chlorhexidine digluconate | 24 grams |
| sodium gluconate | 24 grams |
| deionized water | 952 grams |

The chews were coated at a rate of approximately 114 grams of basting solution per 5 lbs of rawhide. The resulting wet basted chews were dried at 40° C. for 24 hours and subsequently placed in airtight bags.

Example 2

Assay demonstrating rapid solubilization of the therapeutic composition

Rawhide chews (10 grams cut into squares of approximately ¼" on each side) containing the therapeutic composition (e.g., chlorhexidine) were placed in distilled water (20 mls) shaken for 60 seconds, and the resulting filtrate assayed for the presence of chlorhexidine in solution by infrared spectroscopy. Over 80% (0.486 mg/ml) of the theoretical soluble chlorhexidine (0.6 mg/ml) was found in solution. A rawhide chew basted with a solution containing chlorhexidine digluconate but without sodium gluconate showed a soluble chlorhexidine level of only 0.03 mg/ml.

Example 3

Use of different carriers for delivery of a therapeutic agent

Using the assay in Example 2, the therapeutic composition is shown to be effective when administered with a proteinaceous carrier such as a rawhide chew or a food stuff, and furthermore the food stuff may be composed either wholly or partly of protein.

I claim:

1. An antimicrobial animal oral care formulation comprising:

(a) a proteinaceous rawhide chew sufficiently rigid to allow for an oral residence time of at least, approximately, 30 seconds;

(b) a therapeutic composition containing a cationic antimicrobial substance selected from the group consisting of chlorhexidine diacetate, chlorhexidine digluconate and combinations thereof in a saliva soluble form, the composition located proximal to the surface of the chew and maintained proximal to the surface of the chew on the basis of charge attraction; and (c) sodium gluconate, the formulation having approximately equal concentrations of the cationic antimicrobial substance and sodium gluconate, the formulation having at least approximately 0.1 weight %, based upon the weight of the formulation, of the cationic antimicrobial substance proximal to the surface of the chew.

* * * * *